US011737685B2

(12) United States Patent
Abe et al.

(10) Patent No.: US 11,737,685 B2
(45) Date of Patent: Aug. 29, 2023

(54) POSTURE IDENTIFYING DEVICE, POSTURE IDENTIFYING SYSTEM, AND POSTURE IDENTIFYING METHOD

(71) Applicant: TOYOTA BOSHOKU KABUSHIKI KAISHA, Aichi (JP)

(72) Inventors: Hiroki Abe, Aichi (JP); Kenji Kawano, Aichi (JP); Yoshiomi Nishigaki, Aichi (JP)

(73) Assignee: TOYOTA BOSHOKU KABUSHIKI KAISHA, Aichi (JP)

( * ) Notice: Subject to any disclaimer, the term of this patent is extended or adjusted under 35 U.S.C. 154(b) by 449 days.

(21) Appl. No.: 16/890,297

(22) Filed: Jun. 2, 2020

(65) Prior Publication Data

US 2020/0383610 A1 Dec. 10, 2020

(30) Foreign Application Priority Data

Jun. 5, 2019 (JP) .................................. 2019-105413

(51) Int. Cl.
G06T 17/00 (2006.01)
A61B 5/11 (2006.01)
A61B 5/00 (2006.01)

(52) U.S. Cl.
CPC .......... *A61B 5/1116* (2013.01); *A61B 5/4561* (2013.01); *G06T 17/00* (2013.01)

(58) Field of Classification Search
CPC . A61B 5/1116; A61B 5/4561; A61B 2503/22; G06T 17/00
USPC ....................................................... 600/595
See application file for complete search history.

(56) References Cited

U.S. PATENT DOCUMENTS

| | | | |
|---|---|---|---|
| 10,504,264 B1* | 12/2019 | Koenig | G06T 11/001 |
| 2012/0182291 A1* | 7/2012 | Rawat | G06T 17/00 |
| | | | 345/419 |
| 2015/0366350 A1* | 12/2015 | Di Censo | B60N 2/0244 |
| | | | 700/275 |
| 2018/0304774 A1* | 10/2018 | Mizoi | A61B 5/0816 |
| 2019/0118673 A1 | 4/2019 | Kawano et al. | |

FOREIGN PATENT DOCUMENTS

| | | |
|---|---|---|
| JP | 11-64131 | 3/1999 |
| JP | 2016-2456 | 1/2016 |
| JP | 2019-76299 | 5/2019 |

* cited by examiner

*Primary Examiner* — Gordon G Liu
(74) *Attorney, Agent, or Firm* — GREENBLUM & BERNSTEIN, P.L.C.

(57) ABSTRACT

The present disclosure accurately identifies a posture of a user whose body is supported by a supporting apparatus. A posture identifying device includes: a model preparing section configured to prepare a three-dimensional model from body data; a body part position information obtaining section configured to obtain body part position information from a camera; a shape information obtaining section configured to obtain shape information from a shape sensor; a model correcting section configured to correct a posture in the three-dimensional model according to (i) a position of a specific part indicated by the body part position information and (ii) a shape of a seat indicated by the shape information; and a posture identifying section configured to identify a posture of a user from the posture in the three-dimensional model thus corrected.

11 Claims, 9 Drawing Sheets

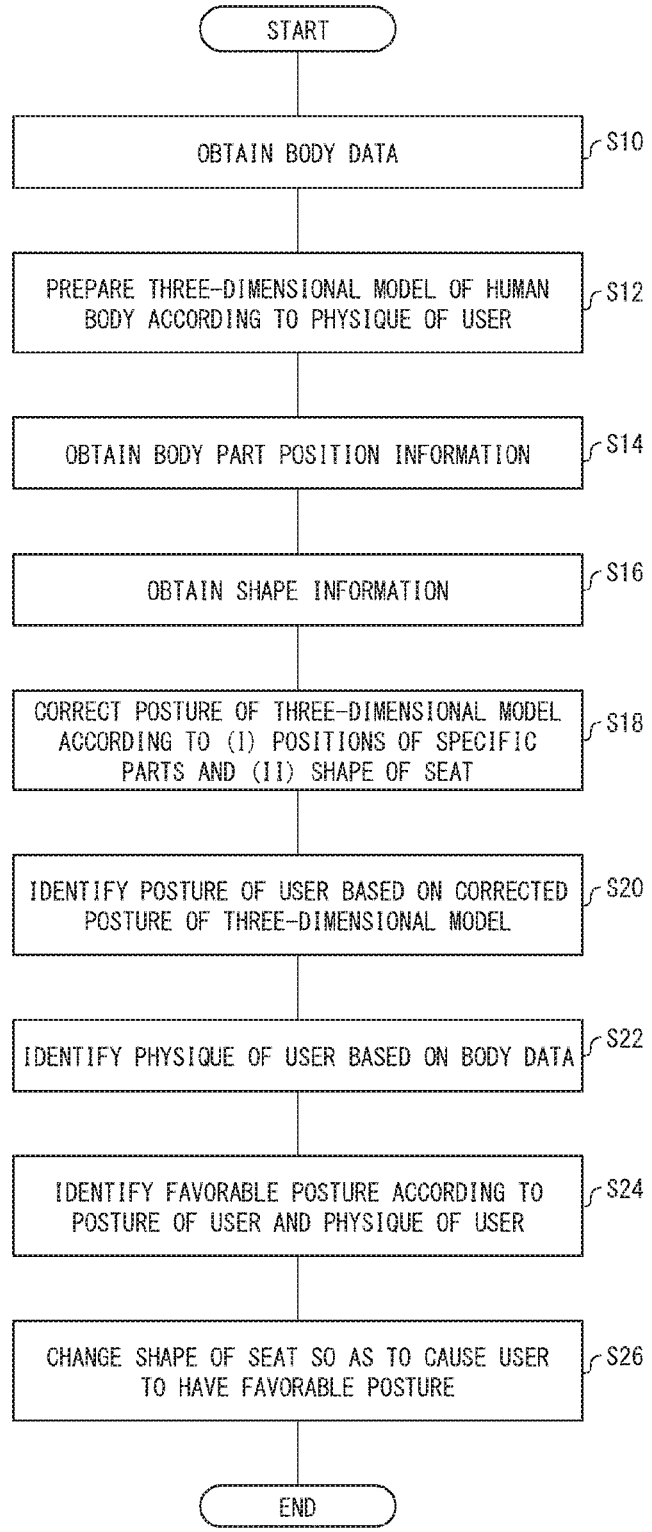

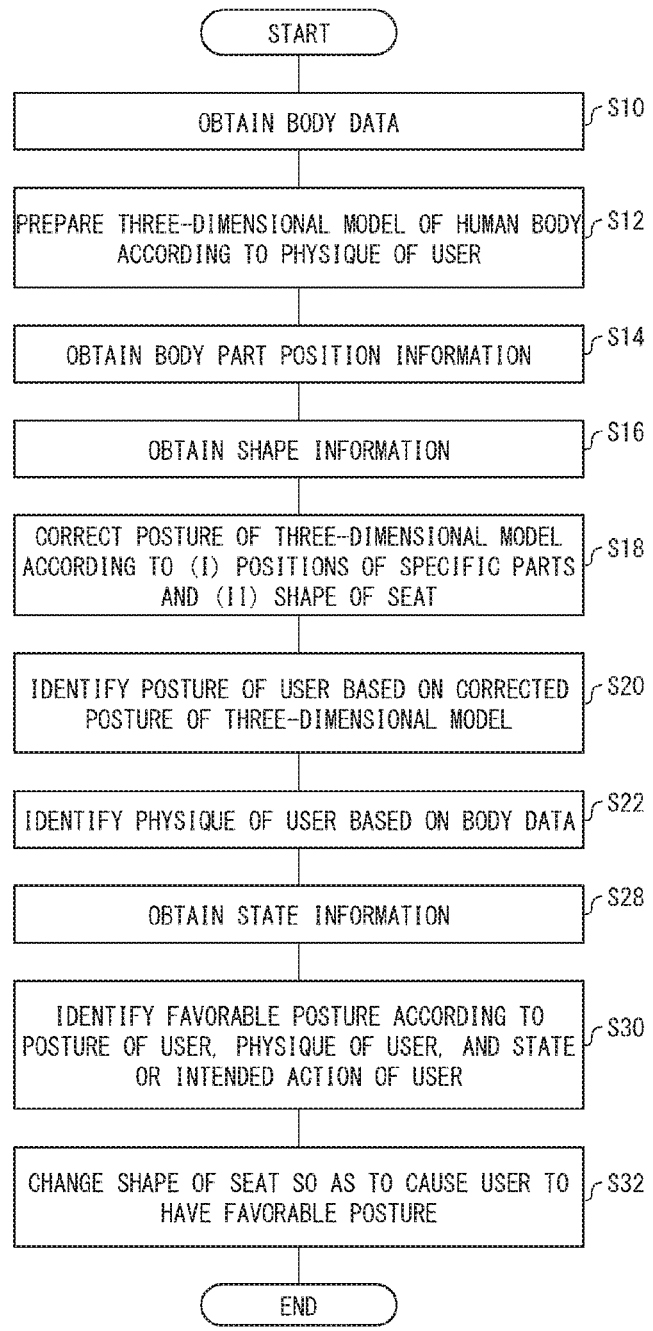

POSTURE IDENTIFYING DEVICE, POSTURE IDENTIFYING SYSTEM, AND POSTURE IDENTIFYING METHOD

This Nonprovisional application claims priority under 35 U.S.C. § 119 on Patent Application No. 2019-105413 filed in Japan on Jun. 5, 2019, the entire contents of which are hereby incorporated by reference.

TECHNICAL FIELD

The present disclosure relates to a posture identifying device, a posture identifying system, and a posture identifying method.

BACKGROUND ART

Conventionally, there have been techniques for identifying a posture of a person sitting on a chair or the like. For example, Patent Literature 1 discloses a technique in which a model, which reflects a posture of a user sitting on a chair, is generated. According to the technique disclosed in Patent Literature 1, the posture of the user is corrected by adjusting various mechanisms of the chair.

CITATION LIST

Patent Literature

[Patent Literature 1]
Japanese Patent Application Publication Tokukai No. 2016-002456

SUMMARY OF INVENTION

Technical Problem

According to the conventional technique, however, the posture is identified without considering differences in physique between individual users when the model is generated. There is therefore a risk of a decrease in accuracy of posture identification, depending on the physique of a user.

An aspect of the present disclosure has been made in view of the problem above. An object of the present disclosure is to achieve a posture identifying device or the like which can accurately identify a posture of a user whose body is supported by a supporting apparatus.

Solution to Problem

In order to attain the object, a posture identifying device in accordance with an aspect of the present disclosure includes: a model preparing section configured to prepare, on the basis of body data indicating a physical characteristic of a user, a three-dimensional model of a human body according to physique of the user; a first information obtaining section configured to obtain, from a first measuring device, first information which indicates a position of a specific part of a body of the user, the body being supported by a supporting apparatus; a second information obtaining section configured to obtain, from a second measuring device included in the supporting apparatus, second information which indicates a shape of the supporting apparatus; a model correcting section configured to correct a posture of the three-dimensional model according to (i) the position of the specific part indicated by the first information and (ii) the shape of the supporting apparatus indicated by the second information; and a posture identifying section configured to identify a posture of the user on the basis of the posture of the three-dimensional model thus corrected by the model correcting section.

In order to attain the object, a posture identifying system in accordance with an aspect of the present disclosure is a posture identifying system including: a posture identifying device; a supporting apparatus; and a first measuring device, the posture identifying device including: a model preparing section configured to prepare, on the basis of body data indicating a physical characteristic of a user, a three-dimensional model of a human body according to physique of the user; a first information obtaining section configured to obtain, from the first measuring device, first information which indicates a position of a specific part of a body of the user, the body being supported by the supporting apparatus; a second information obtaining section configured to obtain, from a second measuring device included in the supporting apparatus, second information which indicates a shape of the supporting apparatus; a model correcting section configured to correct a posture of the three-dimensional model according to (i) the position of the specific part indicated by the first information and (ii) the shape of the supporting apparatus indicated by the second information; and a posture identifying section configured to identify a posture of the user on the basis of the posture of the three-dimensional model thus corrected by the model correcting section. With the configuration above, it is possible to bring about an effect similar to that of the posture identifying device.

In order to attain the object, a posture identifying method in accordance with an aspect of the present disclosure includes the steps of: (a) preparing, on the basis of body data indicating a physical characteristic of a user, three-dimensional model of a human body according to physique of the user; (b) obtaining, from a first measuring device, first information which indicates a position of a specific part of a body of the user, the body being supported by a supporting apparatus; (c) obtaining, from a second measuring device included in the supporting apparatus second information which indicates a shape of the supporting apparatus; (d) correcting a posture of the three-dimensional model according to (i) the position of the specific part indicated by the first information and (ii) the shape of the supporting apparatus indicated by the second information; and (e) identifying a posture of the user on the basis of the posture of the three-dimensional model thus corrected in the step (d). With the process, it is possible to bring about an effect similar to that of the posture identifying device.

Advantageous Effects of Invention

With an aspect of the present disclosure, it is possible to accurately identify a posture of a user whose body is supported by a supporting apparatus.

BRIEF DESCRIPTION OF DRAWINGS

FIG. 7 is a flowchart showing an example of a flow of a process carried out by a posture identifying device included in the posture identifying system.

FIG. 9 is a flowchart showing an example of a flow of a process carried out by a posture identifying device included in the posture identifying system.

DESCRIPTION OF EMBODIMENTS

A posture identifying system in accordance with each embodiment of the present disclosure is a system for identifying a posture of a user whose body is supported by a supporting apparatus. Note that "supporting apparatus" refers to a device, an apparatus, furniture, or the like on which a user can have such a posture as resting his/her body. Examples of the supporting apparatus encompass a seat, a chair, a wheelchair, and a bed. In the following description, a seat including a backrest (seat back) is used as an example of the supporting apparatus. However, the range of applicability of the present disclosure is not limited to a seat.

Embodiment 1

Configuration of Main Parts

Figure 1:
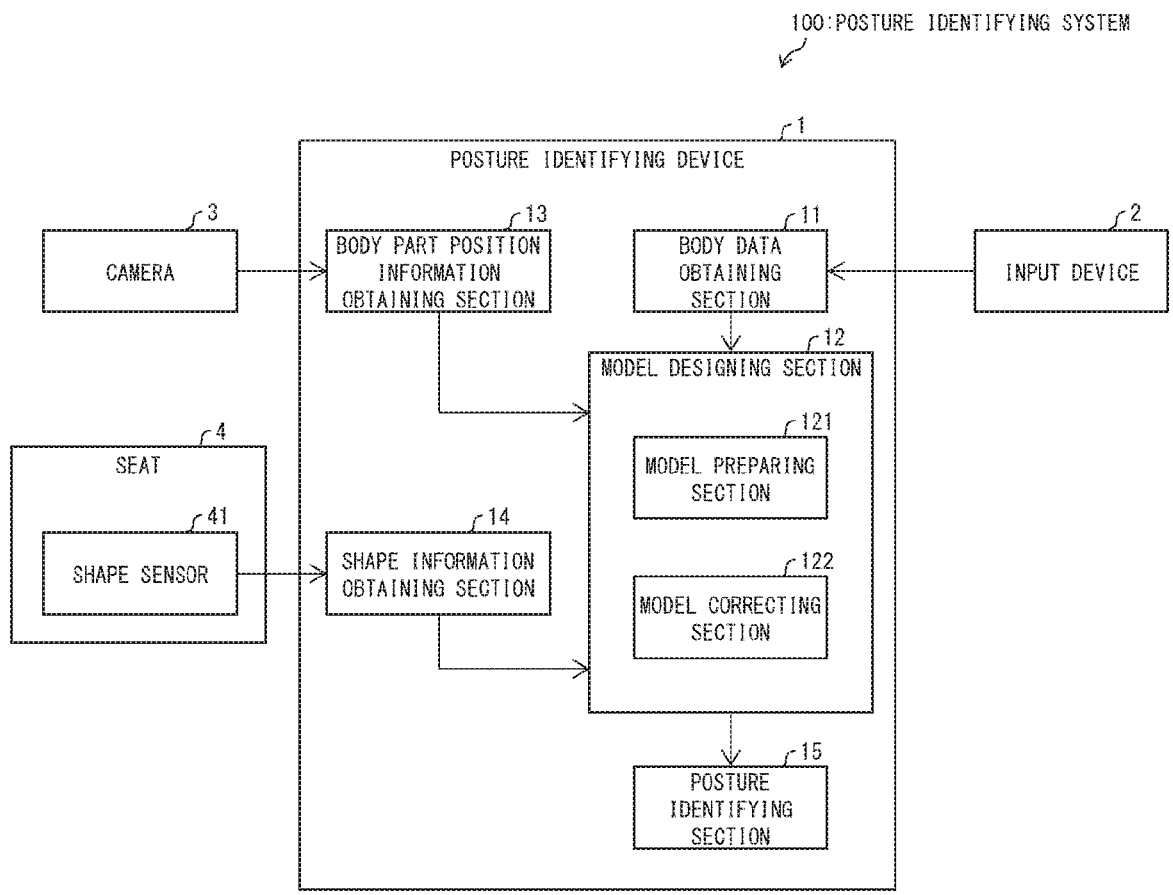
FIG. 1 is a block diagram showing an example of main parts of a posture identifying system in accordance with Embodiment 1 of the present disclosure.

FIG. 1 is a block diagram showing an example of main parts of a posture identifying system 100 in accordance with Embodiment 1. In the example shown in FIG. 1, the posture identifying system 100 includes a posture identifying device 1, an input device 2, a camera (first measuring device) 3, and a seat (supporting apparatus) 4.

Input Device 2

The input device 2 is a user interface (UI) configured to receive an input operation of a user. The input device 2 is achieved by, for example, a touch panel or a physical button. In a case where the input device 2 receives an input operation of a user, the input device 2 supplies a content of the input operation to the posture identifying device 1. For example, the input device 2 receives an input operation for selecting or inputting body data.

Camera 3

The camera 3 is a device configured to capture an image of a user who is sitting on the seat 4. The camera 3 captures an image of the user from a direction and an angle so that at least one specific part of a body of the user is included in the captured image. Then, the camera 3 transmits the captured image to the posture identifying device 1. In other words, the captured image captured by the camera 3 can be regarded as information which indicates a position of a specific part of the body of the user. Hereinafter, information indicating a position of a specific part of a body of a user will be also referred to as "body part position information (first information)".

The type and the number of camera(s) 3 are not particularly limited. In addition, a measuring device other than the camera 3 can be used in the posture identifying system 100 for obtaining body part position information, provided that the body part position information can be used for correction performed by a model correcting section 122 (described later). For example, the posture identifying system 100 can include an infrared sensor instead of the camera 3 or in addition to the camera 3, which infrared sensor is configured to measure a position of a specific part of a body of a user.

Seat 4

The seat 4 is a supporting apparatus configured to support a body of a user. The seat 4 need only have a shape and a size so as to be able to support at least part of the body of the user. According to Embodiment 1, the seat 4 includes a backrest (seat back) and a seating surface which support parts of the user from the head or shoulder to the hips. The seat 4 includes a shape sensor (second measuring device) 41.

The shape sensor 41 is a sensor or a sensor group configured to determine the shape of the seat 4. The type and the number of shape sensor(s) 41 are not particularly limited. Examples of the shape sensor 41 encompass at least one gyro sensor, at least one pressure sensor, at least one position sensor, and a combination of these sensors. In a case where a user sits on the seat 4, the shapes of the seating surface and the seat back change. The shape sensor 41 measures values concerning the shape of the seat 4 which has been thus changed. Note that the shape sensor 41 can measure or calculate values concerning a position of the seat 4.

The shape sensor 41 transmits, as information which indicates the shape of the seat 4, a measurement result or a calculation result to the posture identifying device 1. Hereinafter, the information indicating the shape of the seat 4 will also be referred to as "shape information (second information)". Note that in a case where the shape sensor 41 measures or calculates the values concerning the position of the seat 4, the shape sensor 41 can include information concerning the position of the seat 4 in the shape information to be transmitted to the posture identifying device 1.

In a case where a gyro sensor is employed as the shape sensor 41, it is possible to, for example, attach gyro sensors to the seat back and the seating surface of the seat 4 at certain intervals. This makes it possible to measure angular velocities at parts where the gyro sensors are attached. Then, by continuously measuring the angular velocities for a certain period of time, the gyro sensors can calculate movement angles and movement amounts at the parts where the gyro sensors are attached.

The gyro sensors transmit, as shape information, the calculated movement angles and calculated the movement amounts to the posture identifying device 1. The movement angles and the movement amounts indicate states of deformation of parts of the seat 4 where the gyro sensors are attached. That is, the movement angles and the movement amounts are shape information which indicates the shape of the parts of the seat 4, at which the gyro sensors are attached. In addition, the movement amounts are also information concerning the position of the seat 4.

In a case where a pressure sensor is employed as the shape sensor 41, it is possible to, for example, attach pressure sensors to the seat back and the seating surface of the seat 4 at certain intervals. This makes it possible to measure pressures applied to parts to which the pressure sensors are attached. The pressure sensors each transmit, as the shape information, a measurement result to the posture identifying device 1.

In a case where a position sensor is employed as the shape sensor 41, it is possible to, for example, attach sensors to the seat back and the seating surface of the seat 4 at certain intervals. This makes it possible to measure or calculate directions and movement amounts at parts where the position sensors are attached. To the posture identifying device 1, the position sensors each transmit, as the shape information, the direction and the movement amount thus measured or calculated.

The seat 4 can include a communication section configured to communicate with the posture identifying device 1. Then, instead of or in addition to determining shape information with use of the shape sensor 41, the seat 4 can obtain, from a control mechanism of the seat 4, various parameters concerning controlling of the seat 4. Then, the seat 4 can transmit, as shape information, the various parameters to the posture identifying device 1. Examples of the various parameters encompass) (i) control values of a motor or a cylinder included in the seat 4 and (ii) a pressure value of an air bag included in the seat 4.

Posture Identifying Device 1

The posture identifying device 1 is a device configured to identify a posture of a user sitting on the seat 4. The posture identifying device 1 includes a body data obtaining section 11, a model designing section 12, a body part position information obtaining section (first information obtaining section) 13, a shape information obtaining section (second information obtaining section) 14, and a posture identifying section 15.

The body data obtaining section 11 obtains body data. For example, the body data obtaining section 11 obtains body data which has been inputted by a user via the input device 2. Body data is data which indicates physical characteristics of the user. For example, body data can include data concerning physique of the user.

Note that the body data obtaining section 11 can receive body data from an external device, such as a smartphone, which is capable of communicating with the posture identifying device 1. The body data from the external device can be data inputted into the external device or stored in advance in the external device. Then, the body data obtaining section 11 supplies, to the model designing section 12, the body data thus obtained.

The body part position information obtaining section 13 obtains body part position information. For example, the body part position information obtaining section 13 obtains, as body part position information, a captured image captured by the camera 3. Then, the body part position information obtaining section 13 supplies, to the model designing section 12, the body part position information thus obtained.

The shape information obtaining section 14 obtains shape information. For example, the shape information obtaining section 14 obtains, as shape information, measurement information from the shape sensor 41. Then, the shape information obtaining section 14 supplies, to the model designing section 12, the shape information thus obtained.

The model designing section 12 prepares a digital human model which represents physique of a user. With use of the digital human model, the model designing section 12 simulates a posture of the user. The model designing section 12 includes a model preparing section 121 and the model correcting section 122.

With use of the body data supplied from the body data obtaining section 11, the model preparing section 121 prepares, as a digital human model, a three-dimensional model of a human body according to the physique of the user. Hereinafter, a three-dimensional model of a human body according to physique of a user will also be simply referred to as "three-dimensional model". The model preparing section 121 can also prepare a model of the seat 4, the model representing the size and the shape of the seat 4 on which the user is sitting.

Note that a method, by which the model preparing section 121 prepares the three-dimensional model, is not limited to any particular one. For example, the method of preparing the three-dimensional model can be determined in advance according to the type of information to be obtained as the body data. Alternatively, the model preparing section 121 can change the method as appropriate according to the type of information obtained as the body data.

The model correcting section 122 corrects a posture of the three-dimensional model according to (i) the position of the specific part of the user indicated by the body part position information and (ii) the shape of the seat 4 indicated by the shape information. This simulates the posture of the user sitting on the seat 4.

The model correcting section 122 can process (i) the body part position information supplied from the body part position information obtaining section 13 and (ii) the shape information supplied from the shape information obtaining section 14, so that these pieces of data can be used for the correction of the three-dimensional model. For example, in a case where the body part position information is a captured image captured by the camera 3, the model correcting section 122 can determine a position of the specific part of the user in the captured image by analyzing the captured image.

In a case where the shape information is obtained from a plurality of gyro sensors, the model correcting section 122 can identify the states of deformation (that is, the shapes) of parts of the seat 4, on the basis of the shape information from the respective gyro sensors.

In a case where the shape information is obtained from a plurality of pressure sensors, the model correcting section 122 can identify a pressure distribution of the entire seat 4, based on the shape information from each of the pressure sensors. Then, based on the pressure distribution, the model correcting section 122 can identify the shape of the seat 4 at each part to which a pressure sensor is attached.

In a case where the shape information is obtained from a plurality of position sensors, the model correcting section 122 can identify, based on the shape information from each of the position sensors, a movement amount of the seat 4 at each part to which a position sensor is attached. This allows the model correcting section 122 to identify the shape of the seat 4.

A method, by which the model correcting section 122 corrects the three-dimensional model, can be determined according to the type and the number of specific part(s) indicated by the body part position information. In addition, the method, by which the model correcting section 122 corrects the three-dimensional model, can be determined according to the type of information included in the shape information.

For example, in a case where the body part position information is information which indicates positions of a plurality of specific parts, the model correcting section 122 can correct the posture of the three-dimensional model according to (i) positional relationships between the plurality of specific parts and (ii) the shape of the seat 4. More specifically, in a case where the camera 3 captures an image including an ear, a shoulder, a hip, and a knee of the user, for example, the model correcting section 122 can (1) identify the respective positions of the ear, the shoulder, the hip, and the knee of the user from the image and then (2) correct the posture of the three-dimensional model according to (i) the positional relationships between these parts identified in (1) and (ii) the shape of the seat 4 indicated by the shape information.

With the configuration above, the model correcting section 122 can correct the three-dimensional model in view of the positional relationships between the plurality of specific parts. This allows the model correcting section 122 to accurately correct the three-dimensional model. It is therefore possible for the posture identifying section 15 (described later) to accurately identify the posture of the user.

In a case where, for example, the shape information contains information concerning the position of the seat 4, the model correcting section 122 can correct the posture of the three-dimensional model according to a positional relationship between a specific part and the seat 4. More specifically, it is possible to correct the posture of the three-dimensional model according to the positional relationship between, for example, (i) the position of a shoulder of the user and (ii) a part of the seat 4, which part ordinarily comes into contact with the shoulder.

With the configuration above, the model correcting section 122 can correct the three-dimensional model in view of the positional relationship between the specific part of the user and the seat 4. This allows the model correcting section 122 to accurately correct the three-dimensional model. It is therefore possible for the posture identifying section 15 (described later) to accurately identify the posture of the user.

The process of correcting the posture of the three-dimensional model by the model correcting section 122 will be described in more detail later. The model designing section 12 supplies, to the posture identifying section 15, data which indicates the corrected posture of the three-dimensional model.

The posture identifying section 15 identifies the posture of the user on the basis of the corrected posture of the three-dimensional model. For example, the posture identifying section 15 can identify the type of posture of the user, such as a hunched posture, a standard posture, and an arched-back posture, on the basis of the corrected posture of the three-dimensional model.

Note that other than each block described earlier, the posture identifying device 1 can include a communication section configured to communicate with an external device. The posture identifying device 1 can further include a storage section. The storage section can store at least one of the following: (i) data to be used for preparing a three-dimensional model in the model designing section 12, (ii) a calculation formula for correcting a three-dimensional model, and (iii) body data of a user.

In a case where body data of a user is stored in the storage section in advance, the body data obtaining section 11 can read out the body data from the storage section, instead of obtaining body data from the input device 2. In such a case, the input device 2 is not an essential part of the posture identifying system 100.

Method of Correcting Three-Dimensional Model

An example of the method, by which the model correcting section 122 corrects a three-dimensional model, will be described below with reference to FIG. 2A through FIG. 2D. FIG. 2A through FIG. 2D are a set of views schematically showing an example of the process of correcting a three-dimensional model. In the following description, body part position information contains information which indicates, as specific parts, the following four positions: an ear, a shoulder, a hip, and a knee of a user. In addition., shape information contains information concerning a shape and a position of the seat 4.

Figure 2A:
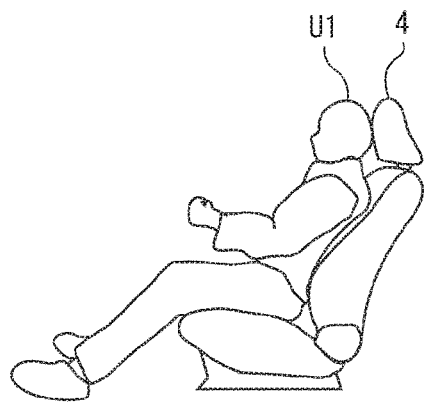
FIG. 2A is a view illustrating a user sitting on a seat.

FIG. 2A is a view illustrating a user U1 sitting on the seat 4. The camera 3 captures an image of the user U1, for example, from the side of the user U1 as illustrated in FIG. 2A so that the specific parts are included in the captured image. The body part position information obtaining section 13 obtains the captured image, and then transmits the captured image to the model designing section 12. In a case where the user U1 sits on the seat 4, the shapes of the seat back and the seating surface of the seat 4 change according to physique and a posture of the user U1. The shape sensor 41 measures the shapes of the seat back and the seating surface thus changed, and then transmits, as the shape information, measurement results to the model designing section 12.

Figure 2B:
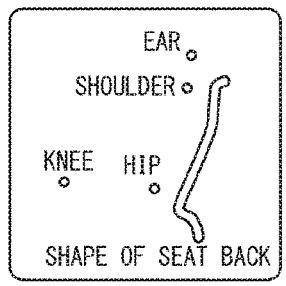
FIG. 2B is a view schematically and two-dimensionally illustrating (i) respective positions of specific parts of a body of the user and (ii) a shape of the seat.

FIG. 2B is a view schematically and two-dimensionally illustrating (i) respective positions of the specific parts of the body of the user and (ii) the shape of the seat 4. In this example shown in FIG. 2B, the shape of the seat back is shown with respect to a direction extending perpendicularly to a direction in which the seating surface extends. In addition, in FIG. 2B through FIG. 2D, the positions of the specific parts of the body of the user and the shape of the seat 4 are two-dimensionally illustrated merely as an example. That is, in a case where the model correcting section 122 corrects a posture of a three-dimensional model, the model correcting section 122 can three-dimensionally calculate (i) the positions of the specific parts of the body of the user and (ii) the shape of the seat 4.

In a case where the shape information contains information concerning the position of the seat 4, the model correcting section 122 identifies coordinates (in the example of FIG. 2B, the position of the seat back) of the seat 4 on the basis of the information concerning the position of the seat 4. Then, the position of the seat 4 and the coordinates of the specific parts of the body of the user are integrally plotted in one coordinate space as illustrated in FIG. 2B. Note that neither a method of integrating the coordinates into the coordinate space nor a coordinate system of the coordinate space is particularly limited, provided that it is possible to plot the coordinates so that the position of the seat 4 and the positions of the specific parts of the body of the user can be recognized relative to each other.

The model correcting section 122 can thus convert, into the coordinates, (i) the positions of the specific parts indicated by the body part position information and (ii) the position of the seat 4 identified on the basis of the shape information. Then, the model correcting section 122 can correct the posture of the three-dimensional model according to the positional relationship between the specific parts and the seat 4, which positional relationship is identified based on the coordinates.

With the configuration above, it is possible to precisely identify the positional relationship between the specific parts and the seat 4 by converting the positions of the specific parts and the position of the seat 4 into such parameters as coordinates.

Figure 2C:
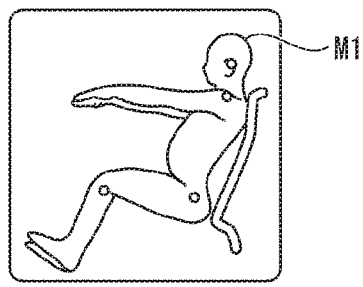
FIG. 2C is a view illustrating a three-dimensional model in a case where positions of an ear, a shoulder, a hip, and a knee of the user illustrated in FIG. 2B are aligned with positions of an ear, a shoulder, a hip, and a knee of a three-dimensional model, respectively.
Figure 2D:
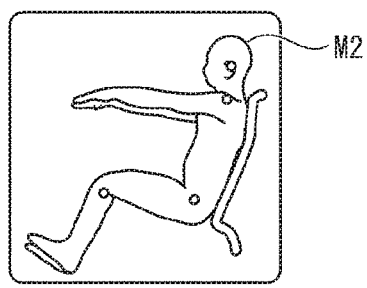
FIG. 2D is a view schematically showing an example of a process of correcting a three-dimensional model.

For example, the model correcting section 122 corrects a three-dimensional model M1 by steps illustrated in FIG. 2C and FIG. 2D. FIG. 2C is a view illustrating a three-dimensional model in a case where the positions of the ear, the shoulder, the hip, and the knee of the user illustrated in FIG. 2B are aligned with the positions of the ear, the shoulder, the hip, and the knee of the three-dimensional model M1, respectively. In the example shown in FIG. 2C, the three-dimensional model M1 has a posture in which the back is unnaturally arched. If specific parts of a user are merely aligned with similar specific parts of a three-dimensional model, then there is a possibility that a posture of sitting on the seat 4, that is, an actual posture of the user may not be reproduced in the three-dimensional model.

Therefore, the model correcting section 122 further corrects the three-dimensional model M1 in the state illustrated in FIG. 2C so that the three-dimensional model M1 corresponds to the shape of the seat 4 identified based on the shape information. For example, the model correcting section 122 corrects the three-dimensional model as illustrated in FIG. 2D.

FIG. 2D is a view illustrating a three-dimensional model M2 in a case where the three-dimensional model M1 illustrated in FIG. 2C has been corrected according to the shape of the seat back. The model correcting section 122 adjusts a position and an angle of each part of the three-dimensional model according to the shape of the seat back. For example, the model correcting section 122 can (i) fix the specific parts aligned in FIG. 2C and then (ii) adjust positions of other feature points (FP) of the three-dimensional model so that the back of the three-dimensional model is in contact with the seat back. This allows the three-dimensional model M1 to be corrected into the three-dimensional model M2 which matches actual positions of the specific parts of the user and corresponds to the shape of the seat 4. Specifically, it is possible to correct the three-dimensional model M1 into the three-dimensional model M2 which has a natural posture of a person sitting on the seat 4.

Flow of Process

Figure 3:
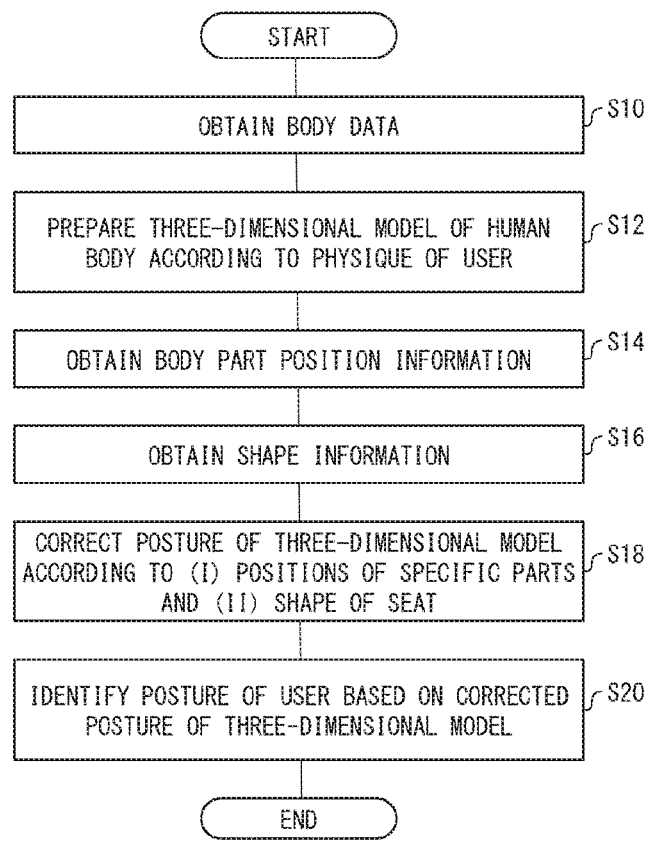
FIG. 3 is a flowchart showing an example of a flow of a process carried out by a posture identifying device included in the posture identifying system.

FIG. 3 is a flowchart illustrating a flow of a process carried out by the posture identifying device 1. Note that in the example shown in FIG. 3, the process is started when body data is inputted via the input device 2. However, the timing of starting the process by the posture identifying device 1 is not limited to such timing.

The body data obtaining section 11 obtains body data which has been inputted via the input device 2 (S10). The body data obtaining section 11 supplies the body data to the model designing section 12. Based on the body data thus inputted, the model preparing section 121 of the model designing section 12 prepares a three-dimensional model of a human body according to physique of a user (S12).

Before or after the steps S10 through S12 or in parallel with the steps S10 through S12, the body part position information obtaining section 13 obtains body part position information from the camera 3 (S14). In addition, the shape information obtaining section 14 obtains shape information from the shape sensor 41 or from the control mechanism of the seat 4 (S16). The step S14 and the step S16 can be carried out in a reverse order or can be carried out in parallel. The body part position information obtaining section 13 supplies the body part position information to the model designing section 12. The shape information obtaining section 14 supplies the shape information to the model designing section 12.

The model correcting section 122 of the model designing section 12 corrects, according to the following (i) and (ii), a posture of the three-dimensional model prepared by the model preparing section 121: (i) positions of specific parts indicated by the body part position information; and (ii) a shape of the seat 4 identified on the basis of the shape information (S18). The model designing section 12 supplies, to the posture identifying section 15, data which indicates the corrected posture of the three-dimensional model.

The posture identifying section 15 identifies the posture of the user on the basis of the corrected posture of the three-dimensional model (S20). For example, the posture identifying section 15 identifies the type of the posture of the user on the basis of the corrected posture of the three-dimensional model.

According to the process described above, the model correcting section 122 corrects, according to the following (i) and (ii), a three-dimensional model which has been prepared according to the physique of the user: (i) the positions of the specific parts identified on the basis of the actual posture of the user sitting on the seat 4 and (ii) the shape of the seat 4. Then, the posture identifying section 15 identifies the posture of the user on the basis of the corrected posture of the three-dimensional model. This allows the posture identifying device 1 to identify postures of users in view of physique of the individual users. It is therefore possible to accurately identify the posture of the user sitting on the seat 4.

Embodiment 2

The following description will discuss another embodiment of the present disclosure. In Embodiment 2 and subsequent embodiments, for convenience, members which are identical in function to the members described in Embodiment 1 will be given identical reference signs, and descriptions of those members will not be repeated.

A posture identifying device in accordance with the present disclosure can include a physique identifying section configured to identify physique of a user on the basis of body data. The posture identifying device in accordance with the present disclosure can further include a favorable posture identifying section configured to identify a favorable posture of a user according to (i) a posture of the user identified by a posture identifying section 15 and (ii) physique of the user identified by the physique identifying section.

Configuration of Main Parts

Figure 4:
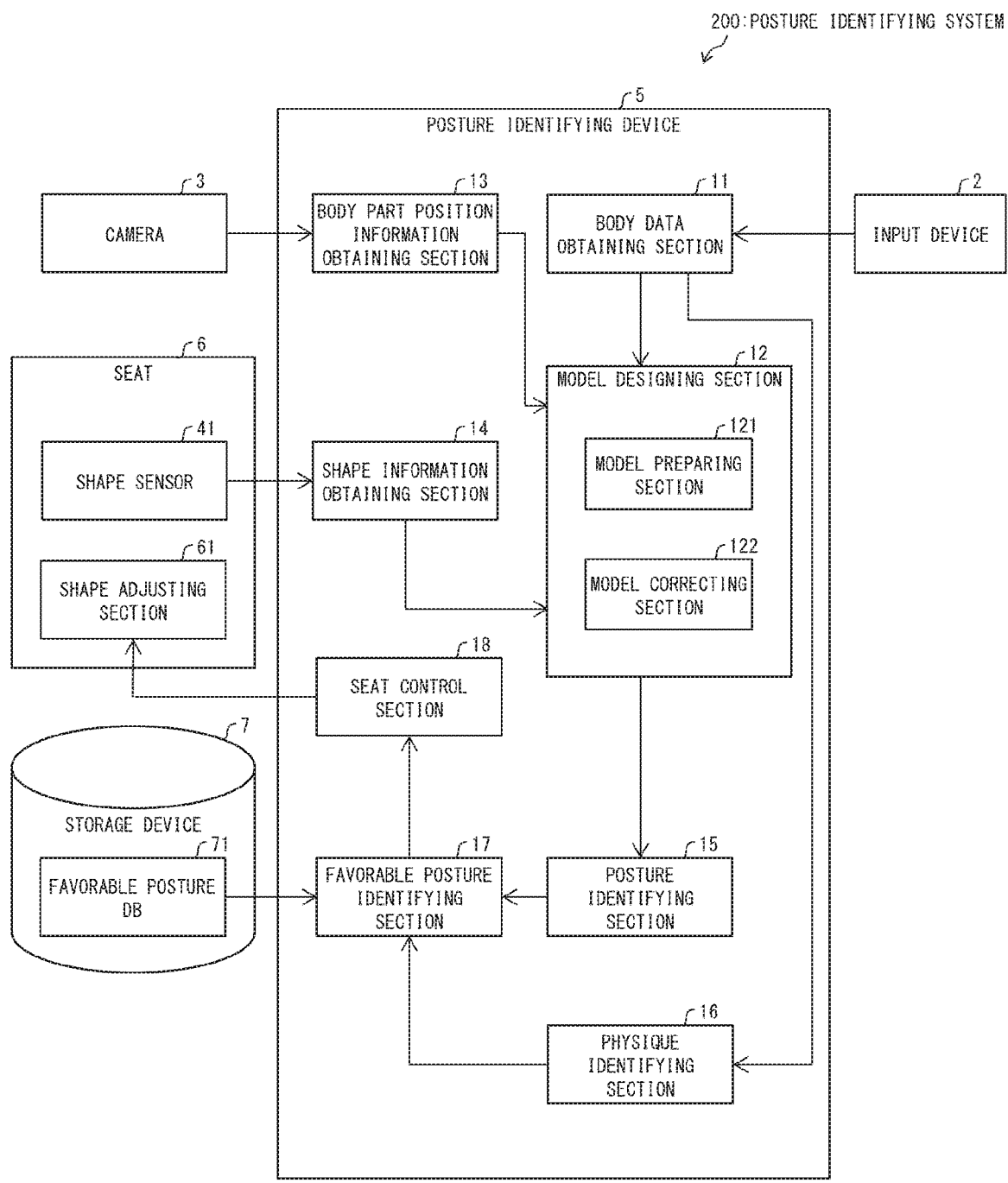
FIG. 4 is a block diagram showing an example of main parts of a posture identifying system in accordance with Embodiment 2 of the present disclosure.

FIG. 4 is a block diagram showing an example of main parts of a posture identifying system 200 in accordance with Embodiment 2. The posture identifying system 200 is different from the posture identifying system 100 in accordance with Embodiment 1 in that the posture identifying system 200 includes a posture identifying device 5, a seat (supporting apparatus) 6, and a storage device 7.

Posture Identifying Device 5

The posture identifying device 5 is different from the posture identifying device 1 in that the posture identifying device 5 includes a physique identifying section 16, a favorable posture identifying section 17, and a seat control section (supporting apparatus control section) 18. The posture identifying device 5 is configured so that a body data obtaining section 11 supplies obtained body data to a model designing section 12 and to the physique identifying section 16. In addition, the posture identifying section 15 supplies, to the favorable posture identifying section 17, information which indicates an identified posture of a user.

Based on the body data, the physique identifying section 16 identifies physique of the user. For example, based on information which is contained in the body data and which concerns physique, the physique identifying section 16 can identify an index value, such as Body Mass Index (BMI), which indicates the physique of the user. Furthermore, based on the index value, the physique identifying section 16 can identify the type of build of the user. Alternatively, from the information concerning the physique of the user, the physique identifying section 16 can directly identify the type of the build of the user. According to Embodiment 2, the physique identifying section 16 identifies, for example, which of "thin", "standard", and "wide" the build of the user fits into.

The favorable posture identifying section 17 identifies a favorable posture of the user according to (i) the posture of the user identified by a posture identifying section 15 and (ii) the physique of the user identified by the physique identifying section 16. A favorable posture means, for example, a posture which does not interfere with an intention of a user and which is comfortable for the user. The favorable posture identifying section 17 can identify the favorable posture by referring to a favorable posture database (DB) 71 which is stored in the storage device (storage section) 7. A data structure of the favorable posture DB 71 will be described in detail later.

The favorable posture identifying section 17 identifies a shape of a seat 6 for causing the user to have the favorable posture thus identified. The favorable posture identifying section 17 supplies, to the seat control section 18, information which indicates the shape of the seat 6 thus identified. For example, the favorable posture identifying section 17 supplies, to the seat control section 18, information concerning control values of the seat 6.

The seat control section 18 then changes the shape of the seat 6 so as to cause the user to have the favorable posture. The seat control section 18 identifies the shape of the seat 6 which corresponds to the favorable posture supplied from the favorable posture identifying section 17. Then, the seat control section 18 instructs a shape adjusting section 61 of the seat 6 to change the shape of the seat 6 from a current shape to the shape corresponding to the favorable posture.

Seat 6

The seat 6 is a supporting apparatus for supporting a body of a user, and is a supporting apparatus having a shape, at least part of which is changeable. The seat 6 is different from the seat 4 in that the seat 6 includes the shape adjusting section 61.

In accordance with the instruction from the posture identifying device 5 (more specifically from the seat control section 18 described later), the shape adjusting section 61 changes the shape of at least part of the seat 6. The shape adjusting section 61 can change the shape of the seat 6 by, for example, changing air pressure inside the seat 6. Alternatively, the shape adjusting section 61 can change the shape of the seat 6 by controlling a mechanism which is provided in the seat 6 and is configured to change the shape.

Storage Device 7

The storage device 7 is a storage device configured to store the favorable posture DB 71. Note that in the example shown in FIG. 4, the storage device 7 is an external device which communicates with the posture identifying device 5. Alternatively, the storage device 7 can be a device embedded in the posture identifying device 5.

Data Structure of Favorable Posture DB 71

The favorable posture DB 71 is a database in which favorable posture data is collected. Favorable posture data means data in which information indicating a favorable posture is associated with a combination of (i) information which indicates the type of physique (i.e. build) of a person and (ii) information which indicates the type of posture when the body of the person is supported by the seat 6.

Figure 5:
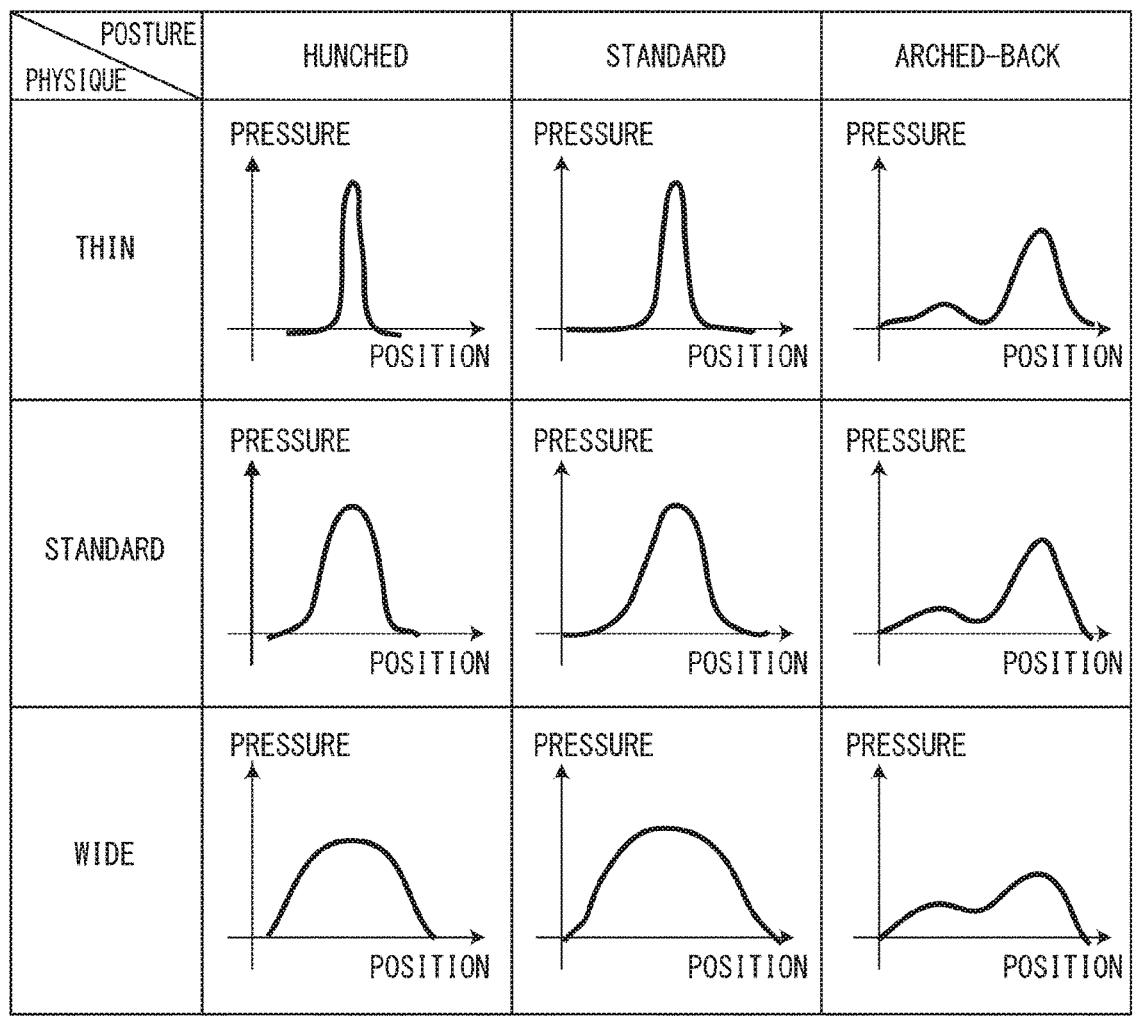
FIG. 5 is a view showing an example of a data structure of a favorable posture database.

FIG. 5 is a view showing an example of the data structure of the favorable posture DB 71. In the example of FIG. 5, the favorable posture DB 71 shows pressure distributions of the seat back of the seat 6 for a favorable posture of a user, which pressure distributions correspond to respective combinations of (1) one of the following three types of physique: "thin", "standard" and "wide" and (2) one of the following three types of posture: "hunched posture", "standard", and "arched-back posture". The x axis in the two-dimensional space in FIG. 5 indicates a position coordinate in a direction extending vertically from the seating surface of the seat back. The origin corresponds to a position of a contact point at which the seating surface and the seat back meet. In addition, the y axis indicates a value of pressure applied to the seat back. The favorable posture identifying section 17 can quickly identify a favorable posture by referring to the favorable posture DB 71 as illustrated in FIG. 5.

Control of Seat 6

The favorable posture identifying section 17 can identify, as coordinates, a shape of the seat 6 for causing a user to have a favorable posture. Then, the favorable posture identifying section 17 can identify a positional relationship between (i) the coordinates and (ii) coordinates of a specific part indicated by body part position information. Then, the favorable posture identifying section 17 can supply, as control values of the seat 6, these coordinates to the seat control section 18.

Figure 6A:
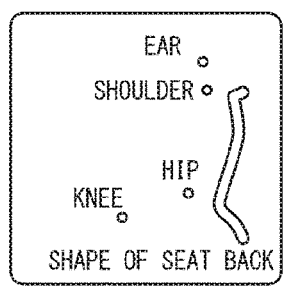
FIG. 6A is a view schematically illustrating a case where the position coordinates of each part of the seat back illustrated in FIG. 2A has been corrected.
Figure 6B:
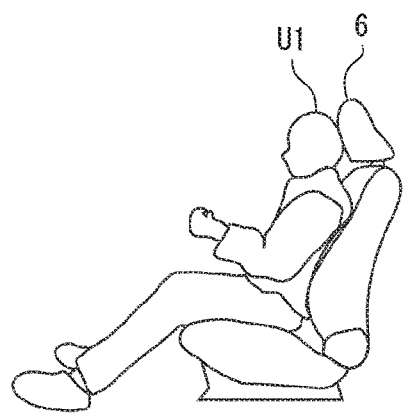
FIG. 6B is a view illustrating a seat and a user in a case where the shape of the seat back illustrated in FIG. 6A is achieved.

FIG. 6A and FIG. 6B are a set of views schematically showing an example of (i) identification of control values of the seat 6 on the basis of a favorable posture and (ii) the seat 6 after the controlling of the seat 6. The favorable posture identifying section 17 identifies pressure values of the seat back of the seat 6 by, for example, referring to the favorable posture DB 71. Then, the favorable posture identifying section 17 corrects, for example, the coordinates of the seat back illustrated in FIG. 2B into coordinates from which the pressure values can be obtained.

FIG. 6A is a view schematically illustrating a case where the position coordinates of each part of the seat back illustrated in FIG. 2A has been corrected by the favorable posture identifying section 17. For example, as illustrated in FIG. 6A, the favorable posture identifying section 17 corrects the position coordinates of each part of the seat back. Note that the favorable posture identifying section 17 may or may not refer to the position coordinates of specific parts of the body of the user. Then, the favorable posture identifying section 17 transmits, as information concerning the control values of the seat back, the corrected coordinates to the seat control section 18.

FIG. 6B illustrates the seat 6 and a user U1 in a case where the shape of the seat back illustrated in FIG. 6A is achieved by the seat control section 18 and by the shape adjusting section 61. By controlling the shape adjusting section 61 so that the seat 6 has the coordinates illustrated in FIG. 6A, the posture identifying device 8 can allow the user to have a favorable posture.

Note that the favorable posture identifying section 17 can supply, to the seat control section 18, pressure values of the respective parts of the seat back identified by referring to the favorable posture DB 71. In addition, the seat 6 can further include a communication section and a pressure sensor. Then, in a case where the shape adjusting section 61 has adjusted the shape of the seat 6, the seat 6 can (i) measure, with use of the pressure sensor, pressure which is applied to each part of the seat 6 (e.g. seat back) and (ii) transmit the measurement values to the seat control section 18.

Then, the seat control section 18 can make a comparison between (i) the pressure values supplied from the seat 6 and (ii) the pressure values supplied from the favorable posture identifying section 17. Then, in a case where there is a difference, by a certain value or more, between the pressure values from the seat 6 and the corresponding pressure values from the favorable posture identifying section 17, the seat control section 18 can transmit a final instruction to the shape adjusting section 61 so as to cancel the difference. Specifically, the seat control section 18 can perform feedback control on the shape adjusting section 61 according to feedback on the pressure values from the seat 6.

Flow of Process

FIG. 7 is a flowchart illustrating a flow of a process carried out by the posture identifying device 5. In FIG. 7, steps given step numbers identical to those in FIG. 3 are identical to those steps in FIG. 3, and the description thereof will therefore not be repeated.

In the posture identifying device 5, the physique identifying section 16 identifies physique of a user on the basis of body data supplied from the body data obtaining section 11 (S22). For example, the physique identifying section 16 identifies which of "thin", "standard", and "wide" types illustrated in FIG. 5 is a type into which the physique of the user fits. Then, the physique identifying section 16 supplies, to the favorable posture identifying section 17, information which indicates the physique thus identified.

The favorable posture identifying section 17 identifies a favorable posture according to (i) information which has been supplied from the posture identifying section 15 and which indicates a posture of the user and (ii) information which has been supplied from the physique identifying section 16 and which indicates the physique of the user (S24). For example, by referring to the favorable posture DB 71, the favorable posture identifying section 17 reads out information which indicates a favorable posture corresponding to a combination, written in the favorable posture DB 71, of (i) the type of the posture of the user and (ii) the type of the physique of the user. In the example of the favorable posture DB 71 illustrated in FIG. 5, the information indicating the favorable posture is data which indicates a pressure distribution of the seat back of the seat 6 which pressure distribution causes the user to have the favorable posture.

Based on the data indicating the favorable posture, the favorable posture identifying section 17 identifies (i) the favorable posture and (ii) a shape of the seat 6 for causing the user to have the favorable posture. The favorable posture identifying section 17 supplies, to the seat control section 18, information which indicates the shape of the seat 6 thus identified. The seat control section 18 provides an instruction to the shape adjusting section 61 of the seat 6 so that the user will have the favorable posture. In this way, the seat control section 18 causes the shape of the seat 6 to be changed (S26).

With the process above, the favorable posture identifying section 17 can identify a favorable posture of a user in view of (i) physique of the user and (ii) a current posture of the user. Then, by changing the shape of the seat 6, it is possible to cause the user to have the favorable posture. This makes it possible to assist the user, who is sitting on the seat 6, to have the favorable posture.

Embodiment 3

A seat 6 of a posture identifying system can be a supporting apparatus provided in a certain space. For example, the seat 6 can be a seat of a moving body. A posture identifying device 5 can include a state information obtaining section 19 configured to obtain state information. The state information is information which indicates (i) a state of a user or (ii) an intended action of the user within a certain space. For example, the state information obtaining section 19 can obtain, as state information, information indicating which of driving, working, resting, and sleeping applies to the state or the intended action of the user. In addition, a favorable posture identifying section 17 can identify a favorable posture according to the state information.

Configuration of Main Parts

Figure 8:
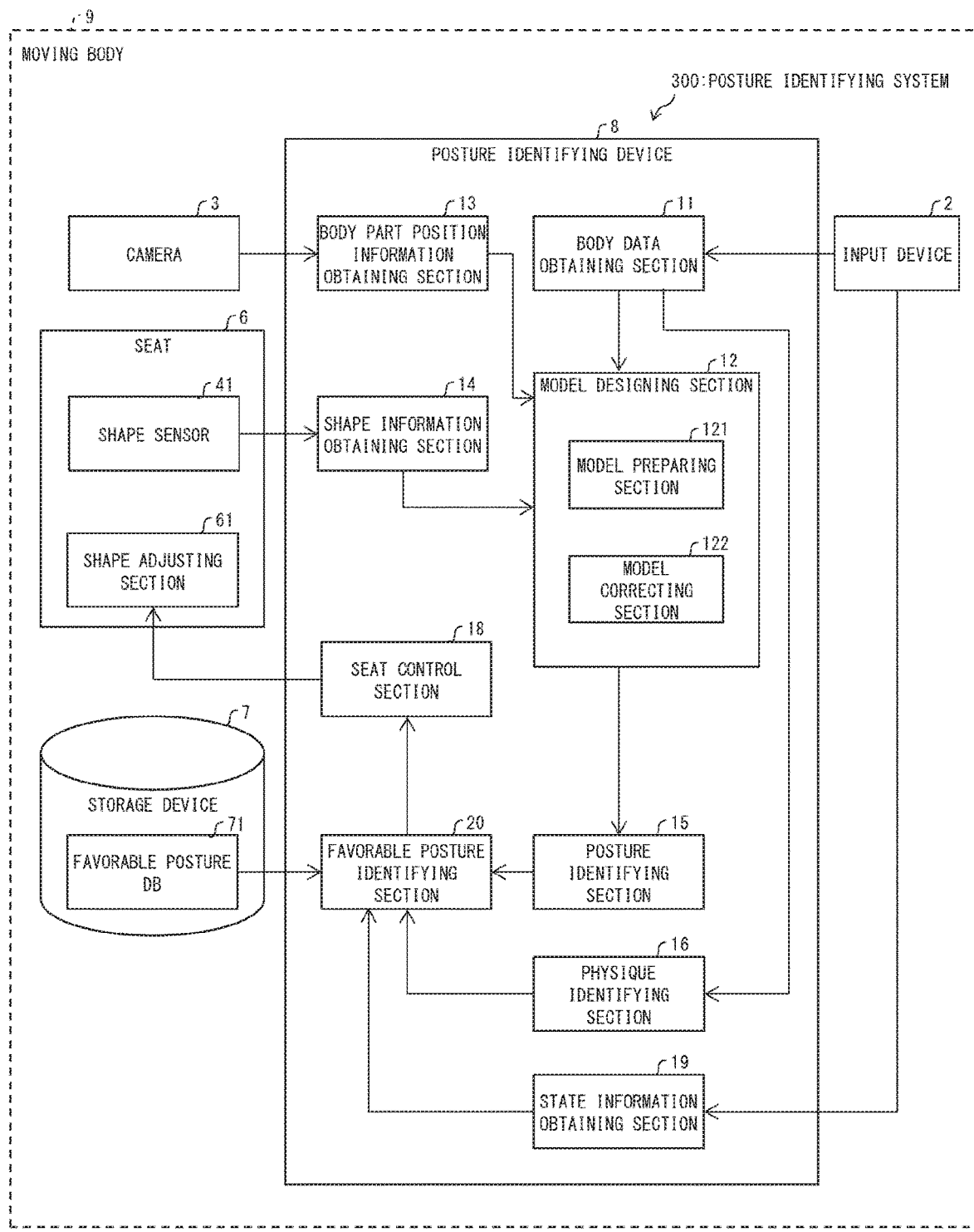
FIG. 8 is a block diagram showing an example of main parts of a posture identifying system in accordance with Embodiment 3 of the present disclosure.

FIG. 8 is a block diagram showing an example of main parts of a posture identifying system 300 in accordance with Embodiment 3. The posture identifying system 300 is different from the posture identifying system 200 of Embodiment 2 in that (i) the posture identifying system 300 includes a posture identifying device 8 and (ii) an input device 2, a camera 3, the seat 6, a storage device 7, and the posture identifying device 8 are provided in a moving body 9.

Moving Body 9

The moving body 9 is a moving body, such as an automobile, a train, a bus, or an airplane, which has a certain space therein. In the inner space of the moving body 9, one or more seats 6 are provided for a passenger of the moving body 9 to sit on. In addition, one or more cameras 3 are provided so as to be able to capture image(s) of the passenger sitting on the one or more seats 6. In the example of FIG. 8, the input device 2, the storage device 7, and the posture identifying device 8 are also provided in the moving body. However, the input device 2, the storage device 7, and the posture identifying device 8 do not necessarily need to be provided in the inner space of the moving body 9, provided that it is possible to communicate with the camera(s) 3 and with the seat(s) 6.

Posture Identifying Device 8

The posture identifying device 8 is different from the posture identifying device 5 in that the posture identifying device 8 includes the state information obtaining section (third information obtaining section) 19 and a favorable posture identifying section 20.

The state information obtaining section 19 obtains state information (third information). The state information is information which indicates (i) a state of a user or (ii) an intended action of the user within a certain space. The state information obtaining section 19 supplies the obtained state information to the favorable posture identifying section 20.

There is no particular limitation on a source from which state information is to be obtained. The state information obtaining section 19 can obtain state information by, for example, the following method. That is, the posture identifying device 8 causes a display section (not illustrated), which is provided in the moving body 9, to display guidance which prompts a user to input a state or an intended action of the user in the moving body 9. Then, in a case where the user inputs information which indicates the state or the intended action of the user via the input device 2, the state information obtaining section 19 obtains the information as state information from the input device 2.

Alternatively, it is possible to allow the user to select a state or an intended action from categories set in advance. For example, it is possible to set the following four categories as categories of the state or the intended action: driving, working, resting, and sleeping. Then, it is possible to allow the user to specify any one from the categories. This makes it possible to identify a favorable posture which corresponds to a category of an action which a user sitting on the seat 6 will presumably perform in the moving body 9. It is therefore possible to identify, as a favorable posture, a posture that is presumably a posture which a user feels favorable.

Note that instead of obtaining state information from the input device 2, the posture identifying device 8 can obtain state information from an external device via a communication section (not illustrated) included in the posture identifying device 8. For example, the posture identifying device 8 can (i) obtain, from a schedule management application in an external device such as a smartphone, information which indicates a schedule of a user and then (ii) identify a state or an intended action of the user. Then, the state information obtaining section 19 can obtain the state of the intended action as state information.

The favorable posture identifying section 20 identifies a favorable posture according to (i) the posture of the user identified by the posture identifying section 15, (ii) the physique of the user identified by the physique identifying section 16, and (iii) the state information obtained by the state information obtaining section 19. Then, the favorable posture identifying section 20 supplies, to the seat control section 18, information which indicates the favorable posture thus identified.

There is no particular limitation on a method by which the favorable posture identifying section 20 deals with state information. However, the favorable posture identifying section 20 can carry out, for example, any of two methods below. A first method is carried out as follows. In a case where state information is to be indicated as a category of a state or an intended action such as driving, working, resting, or sleeping, the storage device 7 is caused to store favorable posture DBs 71 for respective ones of these categories. Then, the favorable posture identifying section 20 identifies a favorable posture by referring to a favorable posture DB 71 which corresponds to the category indicated by the state information.

A second method is carried out as follows. As in the case of the favorable posture identifying section 17, the favorable posture identifying section 20 identifies a favorable posture on the basis of (i) a posture of a user identified by the posture identifying section 15 and (ii) physique of the user identified by the physique identifying section 16. Then, according to the state information, the favorable posture identifying section 20 corrects values for the favorable posture thus identified. For example, in a case where the state information indicates that the state of the user is resting or sleeping, coordinates of each part of the seat 6 for achieving a favorable posture which is temporarily identified can be corrected into coordinates which cause the seat back of the seat 6 to lean further backwards.

Flow of Process

FIG. 9 is a flowchart illustrating a flow of a process carried out by the posture identifying device 8. In FIG. 9, steps given step numbers identical to those in FIGS. 3 and 7 are identical to those steps in FIGS. 3 and 7, and the description thereof will therefore not be repeated.

In the posture identifying device 8, the state information obtaining section 19 obtains state information (S28). Then, the state information obtaining section 19 supplies the state information to the favorable posture identifying section 20. The favorable posture identifying section 20 identifies a favorable posture according to (i) information which has been supplied from the posture identifying section 15 and which indicates a posture of a user, (ii) information which has been supplied from the physique identifying section 16 and which indicates the physique of the user, and (iii) a state or an intended action of the user indicated by the state information (S30). Then, the favorable posture identifying section 20 supplies, to the seat control section 18, information which indicates the favorable posture. More specifically, based on the data indicating the favorable posture, the favorable posture identifying section 20 identifies (i) the favorable posture and (ii) a shape of the seat 6 for causing the user to have the favorable posture. Then, the favorable posture identifying section 20 supplies, to the seat control section 18, information which indicates the shape. The seat control section 18 instructs the shape adjusting section 61 of the seat 6 to change the shape of the seat 6 so that the user will have the favorable posture (S32).

With the process described above, it is possible to identify a favorable posture according to a state or an intended action of a user. It is therefore possible to identify, as a favorable posture, a posture that is presumably a posture which a user feels favorable.

Variations

The posture identifying devices 1, 5, and 8 in accordance with Embodiments 1, 2, and 3, respectively, can each transmit information to an external device via a communication section included in the posture identifying device. Examples of the external device encompass a smartphone of a user. For example, the posture identifying devices 1, 5, and 8 can each transmit, to the external device, a posture (current posture) of the user identified by the posture identifying section 15. In addition, for example, the posture identifying devices 1, 5, and 8 can each transmit, to the external device, information which indicates physique of the user identified by the physique identifying section 16. In addition, for example, the posture identifying devices 1, 5, and 8 can each transmit, to the external device, information which indicates a favorable posture identified by the favorable posture identifying section 17 or 20. In addition, for example, the posture identifying devices 5 and 8 can each transmit, to the external device, information which indicates control values for a case where the seat control section 18 controls the shape adjusting section 61.

Furthermore, the function of the model designing section 12 in each of the posture identifying devices 1, 5, and 8 can be performed by another device such as a server. In such a case, the posture identifying devices 1, 5, and 8 each include a communication section. Then, via the communication section, any one of the posture identifying devices 1, 5, and 8 transmits the following three information/data to the server which performs the function of the model designing section 12: (i) body data obtained by the body data obtaining section 11, (ii) body part position information obtained by the body part position information obtaining section 13, and (iii) shape information obtained by the shape information obtaining section 14. Then, the server performs a process of the model designing section 12 described earlier, and then transmits results of the process to the above one of the posture identifying devices 1, 5, and 8. Specifically, to the above one of the posture identifying devices 1, 5, and 8, the model designing section 12 transmits information which indicates a corrected three-dimensional model. An operation of the above one of the posture identifying devices 1, 5, and 8 after reception of the information is similar to that described in each of the embodiments above.

Software Implementation Example

Control blocks of the posture identifying devices 1, 5, and 8 can be realized by a logic circuit (hardware) provided in an integrated circuit (IC chip) or the like or can be alternatively realized by software.

In the latter case, the posture identifying devices 1, 5, and 8 each include a computer that executes instructions of a program that is software realizing the foregoing functions. The computer, for example, includes at least one processor and at least one computer-readable storage medium storing the program. An object of the present disclosure can be achieved by the processor of the computer reading and executing the program stored in the storage medium. Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. Further, the program may be supplied to or made available to the computer via any transmission medium (such as a communication network and a broadcast wave) which allows the program to be transmitted. Note that an aspect of the present disclosure can also be achieved in the form of a computer data signal in which the program is embodied via electronic transmission and which is embedded in a carrier wave.

Recap

The posture identifying devices, the posture identifying systems, and the posture identifying methods in accordance with the embodiments above can be expressed as follows.

A posture identifying device in accordance with an aspect of the present disclosure includes: a model preparing section configured to prepare, on the basis of body data indicating a physical characteristic of a user, a three-dimensional model of a human body according to physique of the user; a first information obtaining section configured to obtain, from a first measuring device, first information which indicates a position of a specific part of a body of the user, the body being supported by a supporting apparatus; a second information obtaining section configured to obtain, from a second measuring device included in the supporting apparatus, second information which indicates a shape of the supporting apparatus; a model correcting section configured to correct a posture of the three-dimensional model according to (i) the position of the specific part indicated by the first information and (ii) the shape of the supporting apparatus indicated by the second information; and a posture identifying section configured to identify a posture of the user on the basis of the posture of the three-dimensional model thus corrected by the model correcting section.

According to the configuration above, the posture identifying device prepares a three-dimensional model according to the physique of a user, and then corrects the three-dimensional model according to (i) a position of the specific part of the body of the user, the body being supported by the supporting apparatus and (ii) the shape of the supporting apparatus. Then, the posture identifying device identifies the posture of the user on the basis of the corrected posture of the three-dimensional model. This makes it possible to identify postures of users in view of physique of the individual users. It is therefore possible to accurately identify a posture of a user whose body is supported by a supporting apparatus.

The posture identifying device can be configured so that: the first information obtaining section obtains, from the first measuring device, first information which indicates respective positions of a plurality of the specific parts; and the model correcting section corrects the posture of the three-dimensional model according to (i) a positional relationship between the plurality of specific parts and (ii) the shape of the supporting apparatus.

According to the configuration above, the posture identifying device corrects the three-dimensional model in view of the positional relationship between the plurality of specific parts. Then, the posture identifying device identifies the posture of the user on the basis of the corrected three-dimensional model. It is therefore possible to accurately identify the posture of the user.

The posture identifying device can be configured so that: the second information obtaining section obtains, from the second measuring device, second information which contains information concerning a position of the supporting apparatus; and the model correcting section corrects the posture of the three-dimensional model according to a positional relationship between the specific part(s) and the supporting apparatus.

According to the configuration above, the posture identifying device corrects the three-dimensional model in view of the positional relationship between the specific part(s) of the user and the supporting apparatus. Then, the posture identifying device identifies the posture of the user on the basis of the corrected three-dimensional model. It is therefore possible to accurately identify the posture of the user.

The posture identifying device can be configured so that the model correcting section converts, into coordinates, (i) the positions of the specific part(s) indicated by the first information and (ii) the position of the supporting apparatus indicated by the second information, and corrects the posture of the three-dimensional model according to a positional relationship between the specific part(s) and the supporting apparatus, which positional relationship is identified on the basis of the coordinates.

With the configuration above, it is possible to precisely identify the positional relationship between the specific part(s) and the supporting apparatus by converting the position(s) of the specific part(s) and the position of the supporting apparatus into such parameters as coordinates.

The posture identifying device can be configured to further include: a physique identifying section configured to identify the physique of the user on the basis of the body data; and a favorable posture identifying section configured to identify a favorable posture of the user according to (i) the posture of the user identified by the posture identifying section and (ii) the physique of the user identified by the physique identifying section.

With the configuration above, it is possible to identify a favorable posture of a user in view of (i) physique of the user and (ii) a current posture of the user.

The posture identifying device can be configured so that: the supporting apparatus is provided in a certain space; and the posture identifying device includes a third information obtaining section configured to obtain third information which indicates (i) a state of the user or (ii) an intended action of the user in the certain space. In addition, the favorable posture identifying section of the posture identifying device can identify the favorable posture according to the third information.

According to the configuration above, the posture identifying device identifies a favorable posture according to a state or an intended action of a user. This allows the posture identifying device to identify, as a favorable posture, a posture that is presumably a posture which a user feels favorable.

The posture identifying device can be configured so that: the supporting apparatus is a seat of a moving body; and the third information obtaining section of the posture identifying device obtains, as the third information, information indicating which of driving, working, resting, and sleeping applies to the state or the intended action of the user.

With the configuration above, it is possible to identify a favorable posture which corresponds to a category of an action which a user sitting on the seat of the moving body will presumably perform. It is therefore possible to identify, as a favorable posture, a posture that is presumably a posture which the user feels favorable.

The posture identifying device can be configured so that: the shape of the supporting apparatus is changeable; and the posture identifying device includes a supporting apparatus control section configured to change the shape of the supporting apparatus so as to cause the user to have the favorable posture.

With the configuration above, by changing the shape of the supporting apparatus, it is possible to cause a user to have a favorable posture.

The posture identifying device can be configured so that the favorable posture identifying section of the posture identifying device identifies the favorable posture by referring to favorable posture data which is stored in a storage section and in which information indicating the favorable posture is associated with a combination of (i) information indicating the type of physique of a person and (ii) information indicating the type of posture when a body is supported by the supporting apparatus.

With the configuration above, it is possible to identify, with use of favorable posture data, a favorable posture in view of (i) physique of a user and (ii) a current posture of the user. It is therefore possible to quickly identify a favorable posture.

A posture identifying system in accordance with an aspect of the present disclosure includes: the posture identifying device; the supporting apparatus; and the first measuring device. With the configuration above, it is possible to bring about an effect similar to that of the posture identifying device.

A posture identifying method in accordance with an aspect of the present disclosure includes the steps of: (a) preparing, on the basis of body data indicating a physical characteristic of a user, a three-dimensional model of a human body according to physique of the user; (b) obtaining, from a first measuring device, first information which indicates a position of a specific part of a body of the user, the body being supported by a supporting apparatus; (c) obtaining, from a second measuring device included in the supporting apparatus, second information which indicates a shape of the supporting apparatus; (d) correcting a posture of the three-dimensional model according to (i) the position of the specific part indicated by the first information and (ii) the shape of the supporting apparatus indicated by the second information; and (e) identifying a posture of the user on the basis of the posture of the three-dimensional model thus corrected in the step (d). With the process, it is possible to bring about an effect similar to that of the posture identifying device.

The present disclosure is not limited to the embodiments, but can be altered by a skilled person in the art within the scope of the claims. The present disclosure also encompasses, in its technical scope, any embodiment derived by combining technical means disclosed in differing embodiments.

REFERENCE SIGNS LIST 1, 5, 8 Posture identifying device
11 Body data obtaining section
12 Model designing section
121 Model preparing section
122 Model correcting section
13 Body part position information obtaining section (first information obtaining section)
14 Shape information obtaining section (second information obtaining section)
15 Posture identifying section
16 Physique identifying section
17, 20 Favorable posture identifying section
18 Seat control section (supporting apparatus control section)
19 State information obtaining section (third information obtaining section)
2 Input device
3 Camera (first measuring device)
4, 6 Seat (supporting apparatus)
41 Shape sensor (second measuring device)
61 Shape adjusting section
7 Storage device
71 Favorable posture DB
9 Moving body

The invention claimed is:
1. A posture identifying device comprising:
a memory that stores instructions; and
a processor, when executing the instructions stored in the memory, that performs operations including:
preparing, on the basis of body data indicating a physical characteristic of a user, a three-dimensional model of a human body according to physique of the user;

obtaining, from a first measuring device, first information which indicates a position of a specific part of a body of the user, the body being supported by a supporting apparatus including a seatback of a seat;

obtaining, from a second measuring device included in the supporting apparatus, second information which indicates a shape of the supporting apparatus;

correcting a posture of the three-dimensional model according to (i) the position of the specific part indicated by the first information and (ii) the shape of the supporting apparatus indicated by the second information;

identifying a posture of the user on the basis of the corrected posture of the three-dimensional model;

identifying the physique of the user on the basis of the body data; and identifying a favorable posture of the user according to (i) the identified posture of the user and (ii) the identified physique of the user, wherein the posture identifying device further comprises a storage that stores favorable posture data including a plurality of favorable postures, each favorable posture including pressure distribution of the seatback of the seat and being associated with a combination of (i) one of a plurality of physique types including at least thin, standard and wide, and (ii) one of a plurality of posture types including at least a hunched posture, a standard posture and an arched-back posture, the processor identifies one of the plurality of physique types as the physique of the user, the processor identifies one of the plurality of posture types as the posture of the user, and the processor identifies the favorable posture by referring to the favorable posture data stored in the storage and reading one favorable posture including the pressure distribution of the seatback of the seat corresponding to a combination of the identified one of the plurality of physique types and the identified one of the plurality of posture types, to correct the posture of the user.

2. The posture identifying device according to claim 1, wherein the processor performs operations including:

obtaining, from the first measuring device, first information which indicates respective positions of a plurality of the specific parts; and correcting the posture of the three-dimensional model according to (i) a positional relationship between the plurality of specific parts and (ii) the shape of the supporting apparatus.

3. The posture identifying device according to claim 1, wherein the processor performs operations including:

obtaining, from the second measuring device, second information which contains information concerning a position of the supporting apparatus; and correcting the posture of the three-dimensional model according to a positional relationship between the specific part and the supporting apparatus.

4. The posture identifying device according to claim 3, wherein the processor further performs operations including:

converting, into coordinates, (i) the position of the specific part indicated by the first information and (ii) the position of the supporting apparatus indicated by the second information, and correcting the posture of the three-dimensional model according to the positional relationship between the specific part and the supporting apparatus, which positional relationship is identified on the basis of the coordinates.

5. The posture identifying device according to claim 1, wherein:

the supporting apparatus is provided in a certain space;
the processor further performs operations including:
obtaining third information which indicates (i) a state of the user or (ii) an intended action of the user in the certain space; and
identifying the favorable posture according to the third information.

6. The posture identifying device according to claim 5, wherein:

the supporting apparatus is a seat of a moving body; and
the third information includes information indicating which of driving, working, resting, and sleeping applies to the state or the intended action of the user.

7. The posture identifying device according to claim 1, wherein:

the shape of the supporting apparatus is changeable; and
the processor further performs operations including:
changing the shape of the supporting apparatus so as to cause the user to have the favorable posture.

8. The posture identifying device according to claim 1, wherein the processor further receives the body data of the user input by an input operation of the user.

9. The posture identifying device according to claim 8, wherein the body data includes data concerning the physique of the user.

10. A posture identifying system comprising:
a posture identifying device;
a supporting apparatus including a seatback of a seat;
a storage that stores favorable posture data including a plurality of favorable postures, each favorable posture including pressure distribution of the seatback of the seat and being associated with a combination of (i) one of a plurality of physique types including at least thin, standard and wide, and (ii) one of a plurality of posture types including at least a hunched posture, a standard posture and an arched-back posture; and
a first measuring device,
the posture identifying device including:
a memory that stores instructions; and
a processor, when executing the instructions stored in the memory, that performs operations including:
preparing, on the basis of body data indicating a physical characteristic of a user, a three-dimensional model of a human body according to physique of the user;
obtaining, from the first measuring device, first information which indicates a position of a specific part of a body of the user, the body being supported by the supporting apparatus;
obtaining, from a second measuring device included in the supporting apparatus, second information which indicates a shape of the supporting apparatus;
correcting a posture of the three-dimensional model according to (i) the position of the specific part indicated by the first information and (ii) the shape of the supporting apparatus indicated by the second information;
identifying a posture of the user on the basis of the corrected posture of the three-dimensional model;
identifying the physique of the user on the basis of the body data; and identifying a favorable posture of the user according to (i) the identified posture of the user and (ii) the identified physique of the user, wherein the processor identifies one of the plurality of physique types as the physique of the user, the processor identifies one of the plurality of posture types as the posture of the user, and the processor identifies the favorable posture by referring to the favorable posture data stored in the storage and reading one favorable posture including the pressure distribution of the seatback of the seat corresponding to a combination of the identified one of the plurality of physique types and the identified one of the plurality of posture types, to correct the posture of the user.

11. A method of identifying a posture, comprising:

preparing, on the basis of body data indicating a physical characteristic of a user, a three-dimensional model of a human body according to physique of the user;

obtaining, from a first measuring device, first information which indicates a position of a specific part of a body of the user, the body being supported by a supporting apparatus;

obtaining, from a second measuring device included in the supporting apparatus, second information which indicates a shape of the supporting apparatus;

correcting a posture of the three-dimensional model according to (i) the position of the specific part indicated by the first information and (ii) the shape of the supporting apparatus indicated by the second information;

identifying a posture of the user on the basis of the corrected posture of the three-dimensional model;

identifying the physique of the user on the basis of the body data; and identifying a favorable posture of the user according to (i) the identified posture of the user and (ii) the identified physique of the user, wherein favorable posture data is stored in a storage, the favorable posture data including a plurality of favorable postures, each favorable posture including pressure distribution of the seatback of the seat and being associated with a combination of (i) one of a plurality of physique types including at least thin, standard and wide, and (ii) one of a plurality of posture types including at least a hunched posture, a standard posture and an arched-back posture, in identifying the physique of the user, one of the plurality of physique types is identified as the physique of the user, in identifying the posture of the user, one of the plurality of posture types is identified as the posture of the user, and the favorable posture is identified by referring to the favorable posture data stored in the storage and reading one favorable posture including the pressure distribution of the seatback of the seat corresponding to a combination of the identified one of the plurality of physique types and the identified one of the plurality of posture types, to correct the posture of the user.

* * * * *